United States Patent

Abbs et al.

Patent Number: 5,505,207
Date of Patent: Apr. 9, 1996

[54] CHARACTER DISTINGUISHING SIZED BLOOD PRESSURE CUFF SYSTEM

[75] Inventors: Beata J. Abbs, Odessa; Maynard Ramsey, Tampa, both of Fla.

[73] Assignee: Critikon, Inc., Fla.

[21] Appl. No.: 188,971

[22] Filed: Jan. 28, 1994

[51] Int. Cl.$^6$ ................................................. A61B 5/022
[52] U.S. Cl. ....................................................... 128/686
[58] Field of Search ........................... 606/202, 203; 128/686; 40/913, 633, 316, 630, 304, 299, 586; 434/428; 2/244, 246

[56] References Cited

U.S. PATENT DOCUMENTS

| | | | |
|---|---|---|---|
| 2,173,752 | 9/1939 | Carrington | 40/330 |
| 3,765,405 | 10/1973 | Natkanski | 128/686 |
| 4,726,382 | 2/1988 | Boehmer et al. | 128/686 X |
| 4,841,653 | 6/1989 | Negley | 116/335 X |
| 4,901,462 | 2/1990 | Wrigley | 40/299 X |

*Primary Examiner*—Michael H. Thaler

[57] ABSTRACT

A series of blood pressure cuffs is provided having two indications of size thereon. The first indication of size is preferably a sequential system of numbers numbering the size of the cuffs from smallest to largest. The second system of size indication is a caricature depiction of animals of increasing size on each of the respective increasing cuff sizes. For example, five cuffs may be sized from smallest to largest having depicted thereon a goldfish, a rabbit, a duck, a dog and a dinosaur.

4 Claims, 2 Drawing Sheets

CHARACTER DISTINGUISHING SIZED BLOOD PRESSURE CUFF SYSTEM

BACKGROUND OF THE INVENTION

This application relates to blood pressure cuffs for use in noninvasive blood pressure determinations. In particular, this application relates to a size determining system for such blood pressure cuffs. Inflatable bladders in the forms of cuffs are used extensively in determining blood pressure (systolic and diastolic blood pressure). It is well-known that the size of the cuff necessarily affects the determination of blood pressure and therefore appropriate sizing of the cuff is necessary.

For example, U.S. Pat. No. 3,765,405 entitled "Sphygmomanometer Cuff" discloses a series of graduated size cuffs which are used in blood pressure determinations. Each cuff is indexed to a particular size of limb for use. Each of the cuffs is distinguished by having a different color.

SUMMARY OF THE INVENTION

The invention resides in a system of blood pressure cuffs, particularly for neonatal use having pictorial indication of size thereon. That is, in addition to a size indication such a numbering system, a character, cartoon or caricature is imprinted on the cuff. Each cuff in the system is related in size consistent with the relative perceived size of the characters being used. For example, there may be five sizes starting with a goldfish indication, a rabbit indication, a duck indication, a dog indication and finally a dinosaur indication. Thus, it is easy to perceive merely from a view of the caricature the relative size of the respective cuffs.

DESCRIPTION OF THE PREFERRED EMBODIMENT

The present blood pressure cuffs are formed particularly of neonatal size and are formed by example of a soft, inflatable bladder which may be wrapped about a patient's limb and attached to itself by, for example, hook and loop-type fasteners. The bladders are normally provided with two ports, an inflating port and a transducer port. That is, the first port is used for inflating and deflating the cuff during a blood pressure determination and the second port is used to either access a transducer or an appropriate pressure device to produce an indication of pressure within the bladder.

The cuffs have imprinted thereon a size indication in the form of a number which is progressively larger. In the representative example of a five-cuff system, the numbers run from the smallest number 1 to the largest number 5.

Imprinted on the cuffs along with the appropriate numerical indication of size is an indication of size by relative caricature figures such as cartoon figures of animals. In this respect, the relative size of the subjects shown in the cartoon figures indicates the size of the cuff relative to others within the system. As shown in the representative sample, a goldfish is the indication used for the smallest cuff and is the smallest animal selected in the system for representation. The second cuff has a depiction of a rabbit thereon which is larger than the goldfish, but smaller than the next cuff which is given the representation of a duck. The duck, in its own turn, is smaller than the next larger cuff which includes thereon a dog. And finally, the cuff with the indication of the dog is relatively smaller than the larger cuff in the neonatal system which has depicted thereon a dinosaur which is perceived as the largest of the cuffs. These depictions are placed in a section of the cuff immediately adjacent the normal numeric size indication of the cuff. In this way, quick reference, even from a distance, may be made to the size of the cuff through the pictorial representation, and if necessary, confirmation may be had by resort to the numerical representation on the cuff.

Figure 1:
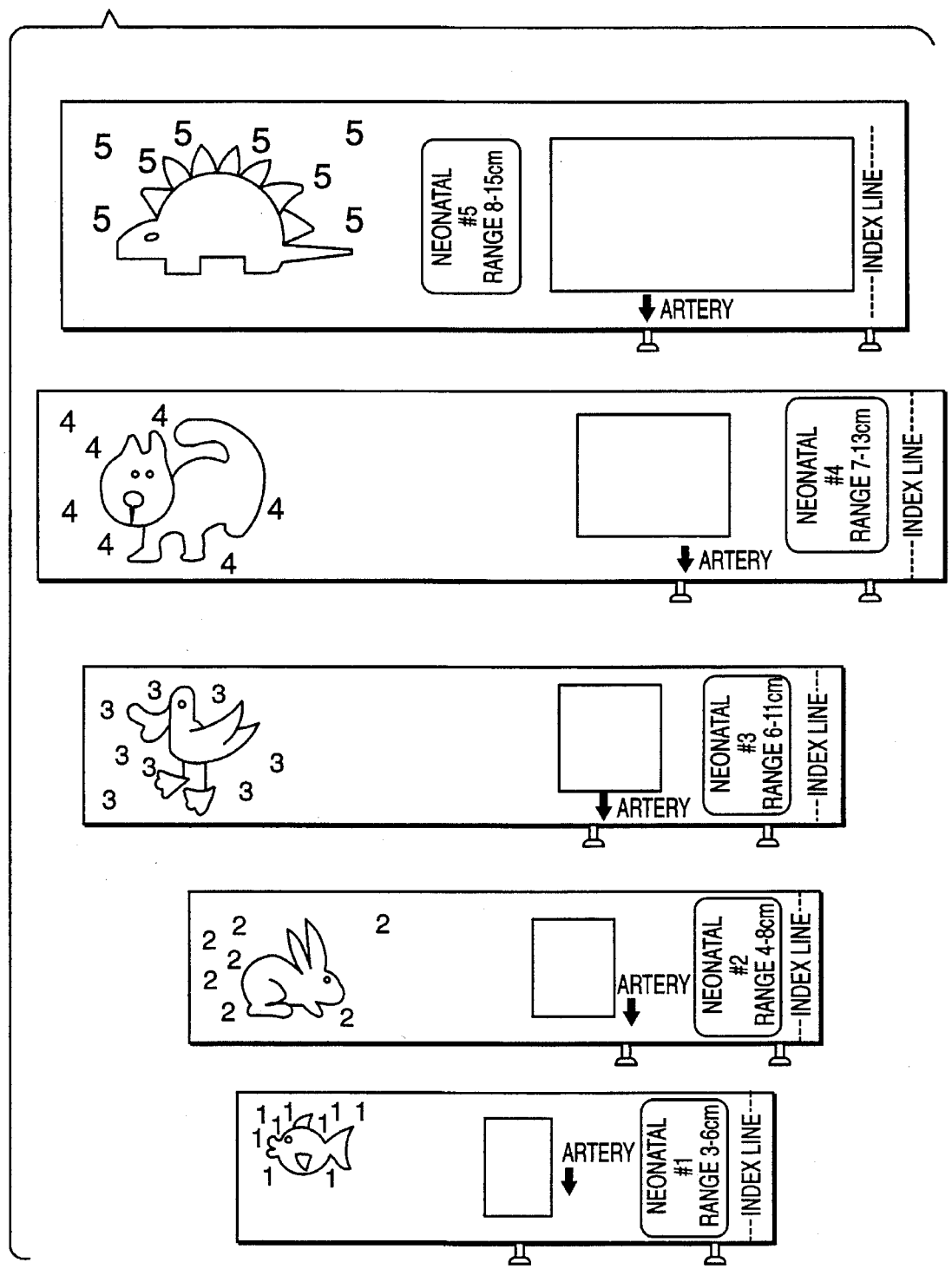
FIG. 1 shows an array of cuffs from the system with size indications thereon both in numbers and in caricature.
Figure 1A:
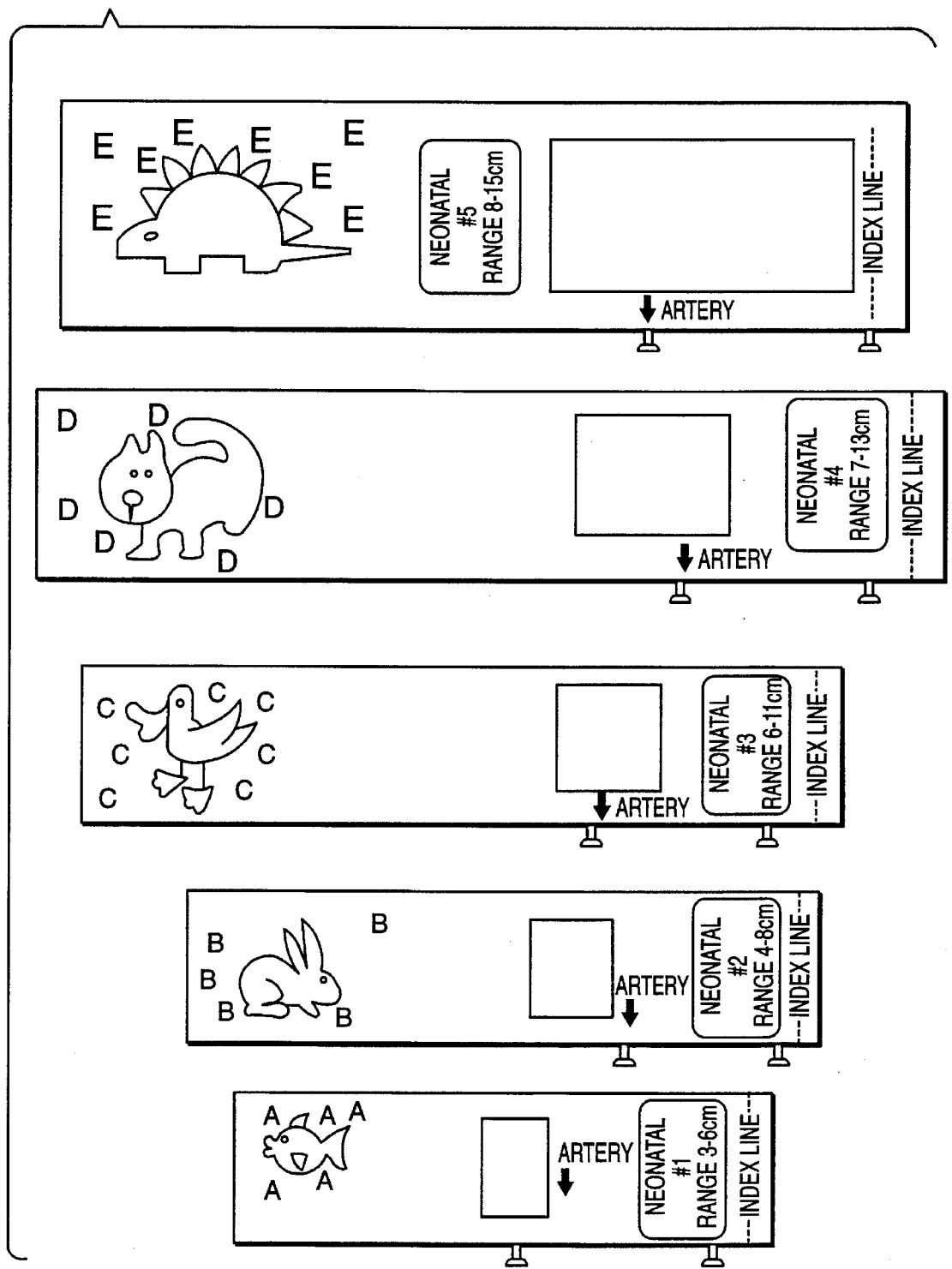
FIG. 1A shows an alternate embodiment of the system depicted in FIG. 1.

The cuffs may be made in any way currently known in the art. Particularly the outer surface must be of a type to accept the character indication by for example transfer printing or silk screening. The selection of character or cartoon should be such that it indicates quickly the relative size of the subject cuff as compared to others in the system. Alternatively the first indication of sizing may be sequential lettering from the arabic alphabet such as A, B, C, D, E. (See FIG. 1A) This is directly analogous to the numerical embodiment.

We claim:

1. A series of blood pressure cuffs of predetermined known serial sizes; each cuff comprising, at least in part, an inflatable bladder having at least one port for inflation and deflation thereof, attachment means provided on the cuff to permit its attachment about the limb of a patient through circumferential wrapping of the limb of the patient, at least two indicators of size on the cuff, a first size indicator being a sequential indication and a second indicator being a size indication provided by predetermined caricatures representing subjects of different size present on the cuffs wherein the second indicator is a series of animal depictions and the animals depicted increase in size as the cuff size increases in size, each of the animals depicted belonging to a different species.

2. The blood pressure cuff according to claim 1 wherein the first indicator is sequential numbering of the blood pressure cuffs.

3. The blood pressure cuff according to claim 1 wherein said first indicator is sequential lettering from the Arabic alphabet.

4. The blood pressure cuff according to claim 1 wherein the animal depictions comprise in part a rabbit, a bird and a dinosaur.

\* \* \* \* \*